United States Patent [19]

Hoefle et al.

[11] 4,350,704
[45] Sep. 21, 1982

[54] SUBSTITUTED ACYL DERIVATIVES OF OCTAHYDRO-1H-INDOLE-2-CARBOXYLIC ACIDS

[75] Inventors: Milton L. Hoefle; George Bobowski, both of Ann Arbor, Mich.

[73] Assignee: Warner-Lambert Company, Morris Plains, N.J.

[21] Appl. No.: 233,940

[22] Filed: Feb. 17, 1981

Related U.S. Application Data

[63] Continuation-in-part of Ser. No. 194,307, Oct. 6, 1980, abandoned, which is a continuation-in-part of Ser. No. 137,106, Apr. 2, 1980, abandoned.

[51] Int. Cl.$^3$ ............... A61K 31/405; C07D 209/34
[52] U.S. Cl. .................................... 424/274; 424/258; 424/262; 424/263; 546/147; 546/170; 546/273; 260/326.13 D; 260/326.13 H; 260/326.12 R
[58] Field of Search ............... 260/326.12 R; 546/147, 546/170, 273; 424/274, 258, 262, 263

[56] References Cited

U.S. PATENT DOCUMENTS

| 3,929,830 | 12/1975 | Richter et al. | 260/326.1 |
|---|---|---|---|
| 4,105,776 | 8/1978 | Ondetti et al. | 260/326.2 |
| 4,116,962 | 9/1978 | Ondetti et al. | 260/326.12 R |
| 4,129,566 | 12/1978 | Ondetti et al. | 260/326 |
| 4,154,840 | 5/1979 | Ondetti et al. | 546/242 |
| 4,154,935 | 5/1979 | Ondetti et al. | 546/189 |
| 4,199,512 | 4/1980 | Ondetti et al. | 260/326.12 R |
| 4,206,121 | 6/1981 | Ondetti et al. | 260/326.12 R |

FOREIGN PATENT DOCUMENTS

| 871574 | 4/1979 | Belgium . |
|---|---|---|
| 873092 | 6/1979 | Belgium . |
| 12401 | 6/1980 | European Pat. Off. . |
| 12845 | 7/1980 | European Pat. Off. . |
| 18104 | 10/1980 | European Pat. Off. . |
| 24852 | 3/1981 | European Pat. Off. . |
| 29488 | 6/1981 | European Pat. Off. . |
| 31741 | 7/1981 | European Pat. Off. . |
| 2720996 | 11/1977 | Fed. Rep. of Germany . |
| 2470767 | 6/1981 | France . |
| 2042535 | 9/1980 | United Kingdom . |

Primary Examiner—Donald G. Daus
Assistant Examiner—James H. Turnipseed
Attorney, Agent, or Firm—Walter Patton

[57] ABSTRACT

Substituted acyl derivatives of octahydro-1H-indole-2-carboxylic acid and the pharmaceutically acceptable salts thereof are produced by acylating a suitably substituted octahydro-1H-indole with a suitably activated substituted carboxylic acid and when desired hydrolyzing the resulting product. The compounds of the invention, their salts and pharmaceutical compositions thereof are useful as antihypertensive agents.

12 Claims, No Drawings

SUBSTITUTED ACYL DERIVATIVES OF OCTAHYDRO-1H-INDOLE-2-CARBOXYLIC ACIDS

This is a continuation-in-part application of copending U.S. patent application Ser. No. 194,307, filed Oct. 6, 1980, now abandoned, which is a continuation-in-part application of copending U.S. patent application Ser. No. 137,106, filed Apr. 2, 1980, now abandoned.

SUMMARY AND DETAILED DESCRIPTION

The invention relates to octahydro-1-($\omega$-mercaptoalkanoyl)-1H-indole-2-carboxylic acid compounds having the formula

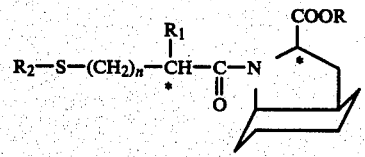

wherein R is hydrogen or lower alkyl; $R_1$ is hydrogen, lower alkyl, or benzyl; $R_2$ is hydrogen or

where $R_3$ is lower alkyl, heteroaryl containing 4 to 9 carbon atoms and one or two nitrogen, oxygen or sulfur atoms; phenyl having 1 or 2 substituents selected from the group consisting of fluorine, chlorine, bromine, lower alkyl, or lower alkoxy; and n is 0 or 1 and pharmaceutically acceptable salts of the compounds when R is hydrogen and when $R_3$ is heteroaryl containing 1 or 2 nitrogen atoms. The terms lower alkyl and lower alkoxy include groups having straight or branched chains and containing 1 to 4 carbon atoms.

The invention further relates to substituted acyl derivatives of octahydro-1H-indole-2-carboxylic acid compounds having the formula

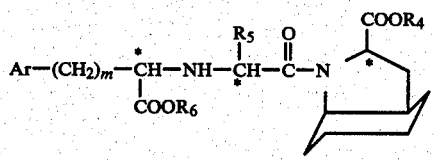

and pharmaceutically acceptable salts thereof therein $R_4$ and $R_6$ are hydrogen or lower alkyl, $R_5$ is hydrogen, lower alkyl or benzyl; Ar is phenyl or phenyl substituted with 1 or 2 substituents selected from the group consisting of fluorine, chlorine, bromine, lower alkyl, lower alkoxy, hydroxy or amino; and m is 0 to 3. The terms lower alkyl and lower alkoxy include groups having straight or branched chains and containing 1 to 4 carbon atoms.

Preferred compounds of the invention are octahydro-1-($\omega$-mercaptoalkanoyl)-1H-indole-2-carboxylic acids having the formula

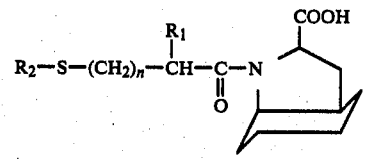

and pharmaceutically acceptable salts thereof; where $R_1$ is hydrogen or lower alkyl containing 1 to 3 carbon atoms; $R_2$ is hydrogen or

where $R_3$ is lower alkyl containing 1 to 3 carbon atoms, phenyl, furyl, benzo(b)furyl, thienyl, benzo(b)thienyl, pyridyl, quinolyl or isoquinolyl; and n is 0 or 1.

Further preferred compounds of the invention are octahydro-1-(3-mercaptopropanoyl)-1H-indole-2-carboxylic acids having the formula

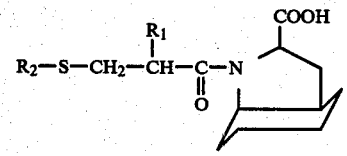

and pharmaceutically acceptable basic salts thereof; where $R_1$ is hydrogen or methyl; and $R_2$ is hydrogen or

where $R_3$ is methyl or phenyl. The preferred specific compounds of the invention are:
octahydro-1-(3-mercaptopropanoyl)-1H-indole-2-carboxylic acid;
octahydro-1-(3-mercapto-2-methylpropanoyl)-1H-indole-2-carboxylic acid;
octahydro-1-[3-(acetylthio)propanoyl]-1H-indole-2-carboxylic acid;
octahydro-1-[3-acetylthio)-2-methylpropanoyl]-1H-indole-2-carboxylic acid
and the pharmaceutically acceptable basic salts thereof.

Also preferred compounds of the invention are acylated octahydro-1H-indole-2-carboxylic acids having the formula

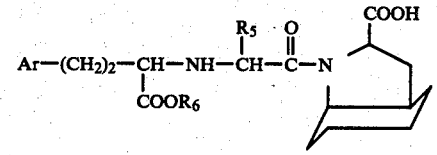

and the pharmaceutically acceptable salts thereof; where $R_5$ is hydrogen or lower alkyl containing 1 to 3 carbon atoms; $R_6$ is hydrogen or lower alkyl containing 1 to 3 carbon atoms; and Ar is phenyl, and phenyl substituted in the para position by fluorine, chlorine, bromine, methyl, hydroxy, methoxy or amino.

Further preferred compounds of the invention are acylated octahydro-1H-indole-2-carboxylic acids having the formula

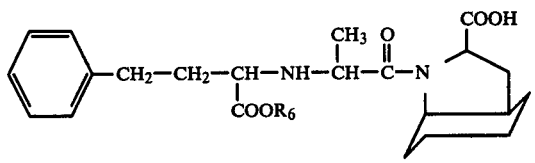

and the pharmaceutically acceptable salts thereof; where R₆ is hydrogen, lower alkyl of 1 to 3 carbon atoms; and specifically the compounds designated 1-[2-[(1-carboxy-3-phenylpropyl)amino]-1-oxopropyl]octahydro-1H-indole-2-carboxylic acid; 1-[2-[(1-carbomethoxy-3-phenylpropyl)amino]-1-oxopropyl]octahydro-1H-indole-2-carboxylic acid; and 1-[2-[(1-carboethoxy-3-phenylpropyl)amino]-1-oxopropyl]octahydro-1H-indole-2-carboxylic acid, and the pharmaceutically acceptable salts thereof.

The compounds of the invention have asymmetric carbon atoms. These carbon atoms are indicated by an asterisk in formula I and II. Additional asymmetric carbon atoms may be present in the lower alkyl groups. The compounds accordingly exist as optical isomers and diastereomers or as racemates and mixtures thereof. All of these are within the scope of the invention.

Single crystal x-ray diffraction analysis of the N-3-bromobenzoyl derivative of octahydro-1H-indole-2-carboxylic acid used as a starting material in this invention has shown that the cyclohexane and pyrrolidine ring junction is the cis configuration, with the carboxylic acid group of the pyrrole ring disposed cis to the fused cyclohexane ring, i.e.,

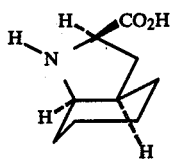

Furthermore, octahydro-1H-indole-2-carboxylic acid has been resolved via the ω-phenylethylamine salt of its N-benzoyl derivative. Biologically active compounds are derived from either the racemic or levorotatory forms of octahydro-1H-indole-2-carboxylic acid. Optical isomers and diastereomers arising from the chirality at the centers marked with an asterisk in formulas I and II and racemates and mixtures thereof are within the scope of this invention. The S configuration at these centers is preferred.

The compounds of the invention may exist in anhydrous form as well as in solvated, including hydrated, forms. In general, the hydrated forms and the solvated forms with pharmaceutically acceptable solvents are equivalent to the anhydrous or unsolvated form for the purposes of the invention.

The compounds of the invention which have the formula

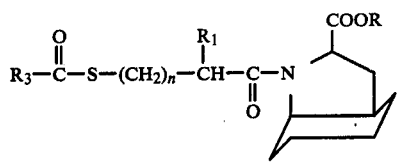

are produced by reacting an octahydro-1H-indole-2-carboxylic acid compound of formula

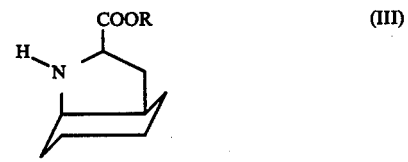 (III)

with an

mercaptoalkanoic acid halide of formula,

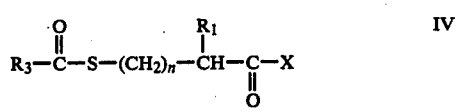 IV in a basic medium; where X is halogen, preferably chlorine or bromine; and R, R₁, R₃ and n have the significance specified above. The basic media can be provided by the use of two molar equivalents of the octahydro-1H-indole-2-carboxylic acid compound or more preferably by the use of an excess of a tertiary organic amine such as pyridine or triethylamine, an alkali or alkaline earth metal hydroxide, an alkali metal bicarbonate, an alkali metal carbonate or other inorganic base capable of neutralizing the hydrogen halide formed during the reaction. The reaction is carried out at a temperature of about 0° C. to about 45° C. under anhydrous or aqueous conditions. Suitable organic solvents for the reaction include dichloromethane, tetrahydrofuran, dioxane, chloroform, pyridine and triethylamine. The reaction is quite rapid and is usually complete in about one-half to four hours.

The compounds of the invention wherein R₂ is an

group and R is hydrogen can, in accordance with the invention, also be produced by reacting a trimethylsilyl ester of a octahydro-1H-indole-2-carboxylic acid with an

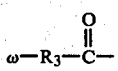

mercaptoalkanoic acid halide (IV) followed by hydrolysis of the intermediate trimethylsilyl ester compound to the free acid by treatment with water. The first step of the process is carried out in a non-protic solvent such as methylene chloride, tetrahydrofuran, dioxane, chloroform or acetonitrile at an elevated temperature, usually about 60° C. to 100° C. After the reaction is complete, about one-half to one hour, the intermediate trimethylsilyl ester compound is treated with water at room temperature to produce the desired product.

The compounds of the invention wherein both R and $R_2$ are hydrogen which have the formula,

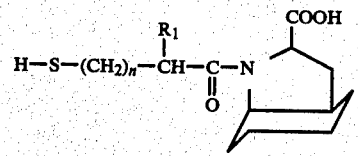

can, in accordance with the invention, be produced by hydrolyzing a compound of the invention which has the formula,

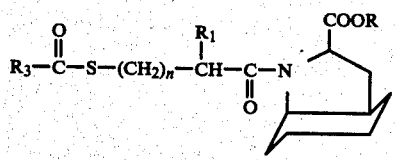

where R, $R_1$, $R_3$ and n have the same significance as given above. The hydrolysis is most conveniently carried out by reacting said compound with an excess of an alkali metal hydroxide in an aqueous alcoholic solution under an inert atmosphere for 5 minutes to 24 hours at a temperature of about 20° C. to about 80° C. The products wherein R and $R_2$ are both hydrogen can also be produced by ammonolysis of a compound of formula,

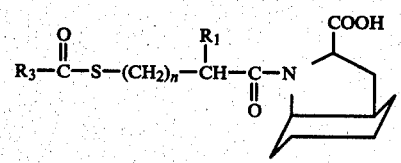

wherein $R_1$, $R_3$ and n have the same significance as given above. The ammonolysis is most conveniently carried out at room temperature in an alcohol which has been saturated with gaseous ammonia. The reaction usually requires 1 to 24 hours for completion.

The above described synthesis can utilize the racemate or one of the enantiomers as starting material. When the racemic starting material is used in the synthetic procedure, the stereomers obtained in the product can be separated by conventional chromatographic or fractional crystallization methods.

Compounds of the invention of formula I where $R_2$ is

may alternately be prepared from compounds where $R_2$ is hydrogen by treatment of the latter with a suitable acylating agent,

where X is a leaving group; e.g., Cl, Br,

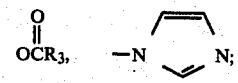

in the presence of a base, e.g., alkali carbonates or tertiary organic amines; in aprotic solvents, e.g., dimethylformamide, tetrahydrofuran or chlorinated hydrocarbons. These may be purified as the free acids or isolated as salts with hindered organic amines, e.g., dicyclohexylamine or t-butylamine.

The compounds of the invention of formula II may be prepared from octahydro-1H-indole-2-carboxylic acid by first protecting the carboxylic acid group, preferably as an ester, e.g., with a lower alkyl, benzyl or trimethylsilyl group. The protected carboxylic acid compound is coupled to an N-protected amino acid, e.g., glycine or L-alanine, protected on nitrogen with t-butyloxycarbonyl or benzyloxycarbonyl. The coupling is carried out by any of a variety of standard peptide coupling techniques as disclosed, for example, in "The Peptides. Analysis, Synthesis, Biology, Vol. 1 Major Methods of Peptide Bond Formation, Part A," ed. E. Gross, J. Meierhofer, Academic Press N.Y. (1979). An especially useful method involves the use of a dehydrating agent, such as dicyclohexylcarbodiimide alone or in the presence of reagents forming reactive esters, e.g., 1-hydroxybenztriazole, in suitable aprotic solvents such as dimethylformamide, acetonitrile, tetrahydrofuran or chlorinated hydrocarbons. This gives the intermediate N-protected-(2-aminoacyl)-octahydro-1H-indole-2-carboxylic acid esters. These may then be either partially or totally deblocked depending on the protecting groups chosen, using anhydrous acids, e.g., hydrochloric acid in acetic acid or trifluoroacetic acid in dichloromethane or hydrogen gas and a catalyst to give the intermediate dipeptide either in free form or protected as an ester.

The compounds of the invention of formula II may then be prepared by reacting the intermediate dipeptide or its ester derivative with α-keto-4-substituted phenylbutyric acid or its lower alkyl ester derivatives under dehydrating and reducing conditions. Preferred dehydrating agents include molecular sieves in aprotic solvents and preferred reducing agents include sodium cyanoborohydride or hydrogen gas with a catalyst.

Alternatively, the dipeptide or its ester derivative may be reacted with an α-halo-4-substituted phenylbutyric acid or its ester in the presence of a suitable basic reagent, such as triethylamine or alkali carbonates or bicarbonates, in a solvent, to give the compounds of the invention of formula II. Ester protected products may be hydrolyzed under basic or acidic reaction conditions to free acid derivatives, or, in the case of benzyl esters, catalytic hydrogenolysis may be preferred.

Alternately, compounds of the invention of formula II may be prepared in a different manner. This consists of applying either of the two methods described above for the attachment of the 2-(4-phenylbuyric acid) moiety to the protected dipeptide, first to glycine or L-alanine, protected as an ester, to give N-[2-(4-phenylbutric acid)]-substituted glycine or L-alanine derivative.

After selective deblocking of the acid moiety on the glycine or alanine portion of the product, the resulting monoacid may be coupled, either directly or subsequent to suitable blocking of the amino group, via standard peptide coupling procedures to the octahydro-1H-indole-2-carboxylic acid, protected as an ester, i.e., $R_7$. Selective or complete removal of the ester groups and any amine protecting groups yield the compounds of formula II.

The products are obtained typically as a mixture of diastereomers which can be separated by standard methods of fractional crystallization or chromatography. The compounds of this invention form basic salts with various inorganic and organic bases which are also within the scope of the invention. Such salts include ammonium salts, alkali metal salts like sodium and potassium salts, alkaline earth metal salts like the calcium and magnesium salts, salts with organic bases, e.g., dicyclohexylamine or benzathine, salts with basic amino acids like arginine, lysine and the like. The pharmaceutically acceptable salts are preferred, although other salts such as the dicyclohexylamine salt are also useful, e.g., in isolating, purifying or characterizing the product.

The salts are formed in conventional manner by reacting the free acid form of the product with one or more equivalents of the appropriate base providing the desired cation in a solvent or medium in which the salt is insoluble, or in water and removing the water by freeze drying.

In the compounds of formula I when $R_3$ is heteroaryl containing 1 or 2 nitrogen atoms and in the compounds of formula II the pharmaceutically acceptable acid addition salts may be prepared by conventional reactions with equivalent amounts of organic or inorganic acids. As exemplary, but not limiting, of pharmaceutically acceptable acid salts are the salts of hydrochloric, sulfuric, acetic, fumeric, malic, maleic and citric acids.

The action of the enzyme renin on angiotensinogen, a pseudoglobulin in blood plasma, produces the decapeptide angiotensin I. Angiotensin I is converted by angiotensin converting enzyme (ACE) to the octapeptide angiotensin II. The latter is an active pressor substance which has been implicated as the causative agent in various forms of hypertension in various mammalian species, e.g., rats and dogs. The compounds of this invention intervene in the renin→angiotensin I→angiotensin II sequence by inhibiting angiotensin I converting enzyme and reducing or eliminating the formation of the pressor substance angiotensin II, and therefore are useful in reducing or relieving hypertension. Thus by the administration of a composition containing one or a combination of compounds of formula I or a pharmaceutically acceptable salt thereof, hypertension in the species of mammal suffering therefrom is alleviated. A single dose, or preferably two to four divided daily doses, provided on a basis of about 0.1 to 100 mg per kilogram per day, preferably about 1 to 50 mg per kilogram per day is appropriate to reduce blood pressure. The substance is preferably administered orally, but parenteral routes such as subcutaneously, intramuscularly, intravenously or intraperitonealy can also be employed.

The following Table shows the in vitro activity of compounds of formula V and VI in an assay for angiotensin converting enzyme inhibitory activity which is a modification of a test reported by D. Cushman and H. Cheung, Biochemical Pharmacology, 20, 1637–1648 (1971).

In vitro ACE Assay: Angiotensin converting enzyme (ACE) inhibitory activity is determined by assaying guinea pig serum ACE in the presence and absence of the test compound. ACE from guinea pig serum and the test compounds are preincubated for 10 minutes before the addition of the labelled substrate $^3$H-hippuryl-glycylglycine. After a 60 minute incubation at 37° C. the reaction is stopped by the addition of 0.1 N HCl. ACE cleaves the hippuryl-glycyl bond to form the dipeptide glycyl-glycine and $^3$H-hippuric acid. The $^3$H-hippuric acid is then extracted with ethyl acetate and the ACE inhibition of a given sample calculated on the basis of the $^3$H-hippuric acid generated.

TABLE
Activity of Compounds of Formula V

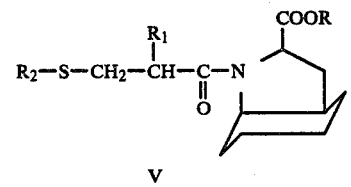

V

| R | $R_1$ | $R_2$ | Diastereoisomer | $IC_{50}$ Molar Conc. |
|---|---|---|---|---|
| $C_2H_5$ | H | $CH_3CO-$ | — | $3.8 \times 10^{-6}$ |
| H | H | H | — | $2.1 \times 10^{-8}$ |
| H | H | $CH_3CO-$ | — | $4.5 \times 10^{-7}$ |
| $C_2H_5$ | $CH_3$ | $CH_3CO-$ | — | $6.7 \times 10^{-6}$ |
| H | $CH_3$ | H | — | $1.6 \times 10^{-8}$ |
| H | $CH_3$ | $CH_3CO-$ | A | $1.6 \times 10^{-7}$ |
| H | $CH_3$ | $CH_3CO-$ | dl, B | $1.1 \times 10^{-6}$ |
| H | $CH_3$ | H | dl, A | $7.0 \times 10^{-9}$ |
| H | $CH_3$ | $CH_3CH_2CO$ | dl, A | $5.2 \times 10^{-8}$ |
| H | $CH_3$ | $(CH_3)_3CCO$ | dl, A | $1.7 \times 10^{-7}$ |
| H | $CH_3$ | PhCO | dl, A | $9.6 \times 10^{-7}$ |
| H | H | $(CH_3)_3CCO$ | dl | $5.8 \times 10^{-8}$ |
| H | H | $CH_3CO$ | l | $4.8 \times 10^{-7}$ |
| H | H | H | l | $6.4 \times 10^{-9}$ |
| H | $CH_3$ | H | l, A | $5.2 \times 10^{-9}$ |
| H | $CH_3$ | PhCO | l, A | $5.4 \times 10^{-7}$ |

TABLE
Activity of Compounds of Formula VI

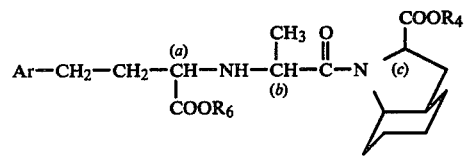

VI

| Ar | $R_6$ | $R_4$ | VI configuration at (a) | (b) | (c) | $IC_{50}$ (Molar Conc.) |
|---|---|---|---|---|---|---|
| Ph | $C_2H_5$ | H | S | S | RS | $2.4 \times 10^{-7}$ |
| Ph | $C_2H_5$ | H | S | S | S | $7.2 \times 10^{-8}$ |
| Ph | H | H | S | S | RS | $6.2 \times 10^{-9}$ |
| Ph | H | H | S | S | S | $2.3 \times 10^{-9}$ |

The $IC_{50}$ is the molar concentration of compound which inhibits 50% of the conversion of angiotensin I to angiotension II.

The compounds of the invention can be utilized to reduce blood pressure in the form of tablets, capsules or elixirs for oral administration or in sterile solutions or suspensions for parenteral administration. About 10 to 500 mg. of a compound or mixture of compounds of formula I or II or a pharmaceutically acceptable salt thereof is compounded with a pharmaceutically acceptable vehicle or carrier which may contain excipients, binders, preservatives, stabilizers, flavors, etc., in accord with accepted pharmaceutical practice. The amount of active substance in these compositions or preparations is such that a suitable dosage in the range indicated is obtained.

Illustrative of the inert ingredients which may be incorporated in tablets, capsules and the like are the following: A binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type a liquid carrier such as a fatty oil. Various other materials may be present as coating or to otherwise modify the physical form of the dosage unit. For instance, tablets may be coated with shellac, sugar or both. A syrup or elixir may contain the active compound, sucrose as a sweentening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The invention is illustrated by the following examples.

EXAMPLE 1

Ethyl (2α, 3aβ, 7aβ)-Octahydro-1-[3-(acetylthio)propanoyl]-1H-indole-2-carboxylate.

A solution of 4.2 g (0.025 mole) of 3-(acetylthio)propanoyl chloride in 10 ml of dichloromethane is added over a period of 20 minutes to a stirred mixture of 4.9 g (0.025 mole) of racemic ethyl (2α, 3aβ, 7aβ)-octahydro-1H-indole-2-carboxylate and 4.0 g of sodium bicarbonate in 40 ml of water and 90 ml of dichloromethane at 5° to 10° C. with cooling. After 40 minutes the two phases are separated and the aqueous phase extracted with 50 ml of dichloromethane. The combined organic extracts are washed first with dilute sulfuric acid (0.01 N), then sodium bicarbonate (0.01 N), and finally water. The organic layer is separated and dried over sodium sulfate. The solvent is removed in vacuo giving 5.8 g of product as a viscous colorless liquid, b.p. 245°–247° C. (753 mm). Infrared (film): 1745 (ester C=O), 1690 (S-acetyl C=O), 1643 cm$^{-1}$ (amide C=O). Tlc (2:1 acetonitrile-methanol/SiO$_2$) single spot, R$_f$ 0.3.

Anal. Calcd. for C$_{16}$H$_{25}$NO$_4$S: C, 58.70; H, 7.70; N, 4.28. Found: C, 58.17; H, 7.69; N, 4.00.

The ethyl (2α, 3aβ, 7aβ)-octahydro-1H-indole-2-carboxylate used as the starting material in Example 1 is prepared by the following procedure. A solution of 100 g (0.53 mole) of ethyl indole-2-carboxylate in 1000 ml of absolute ethanol and 32 ml of concentrated sulfuric acid is hydrogenated over rhodium on charcoal (4.0 g; 10%) using a Paar hydrogenation apparatus until the uptake of hydrogen ceases (22.3 hours). The catalyst is removed by filtration, and the filtrate is evaporated in vacuo. The sirupy residue is dissolved in ice water and the solution is neutralized first with potassium carbonate and then made basic with potassium bicarbonate. The oily precipitate is extracted with 300 ml diethyl ether, and the aqueous layer is extracted with another 300 ml of diethyl ether. The combined ethereal extracts are washed with saturated aqueous sodium chloride solution, dried over sodium sulfate and evaporated in vacuo yielding 78.5 g of ethyl (2α, 3aβ, 7aβ)-octahydro-1H-indole-2-carboxylate as a nearly colorless oil of high purity. The original aqueous layer is saturated with solid sodium chloride and extracted twice with 150 ml of ethyl acetate. The combined extracts are washed with a small amount of water, dried over sodium sulfate and evaporated in vacuo to yield an additional 6.5 g of product. Infrared (film): 3450, 3300 (NH), 1732 cm$^{-1}$ (ester C=O). n$_D^{25}$ = 1.4767. This material is sufficiently pure to be used directly in the example above.

EXAMPLE 2

(2α, 3aβ, 7aβ)-Octahydro-1-(3-mercaptopropanoyl)-1H-indole-2-carboxylic Acid.

A suspension of 2.0 g of ethyl (2α, 3aβ, 7aβ)-octahydro-1-[3-(acetylthio)propanoyl]-1H-indole-2-carboxylate in 10 ml of 10% aqueous sodium hydroxide is allowed to stand at room temperature overnight under nitrogen. The resulting solution is made acidic by the addition of glacial acetic acid to pH 6.0. The resulting gummy precipitate is extracted twice with 100 ml of diethyl ether. The combined ethereal extracts are washed with saturated sodium chloride solution, dried over sodium sulfate and evaporated under nitrogen. Trituration of the residue with warm acetonitrile and cooling yields 1.6 g of product; mp 143°–144° C. A highly pure sample is obtained by recrystallization from acetonitrile; mp 145°–146° C. Infrared (KBr): 2615 (SH); 1735 (COOH); 1597 cm$^{-1}$ (amide C=O).

Anal. Calcd. for C$_{12}$H$_{19}$NO$_3$S: C, 56.02; H, 7.44; N, 5.44. Found: C, 56.33; H, 7.46 N, 5.43.

EXAMPLE 3

(2α, 3aβ, 7aβ)-Octahydro-1-[3-(acetylthio)propanoyl]-1H-indole-2-carboxylic Acid.

(a) 3-(Acetylthio)propanoyl chloride (4.2 g; 0.025 mole) is added dropwise at −5° to 0° C. to a vigorously stirred solution of 4.2 g (0.025 mole) of (2α, 3aβ, 7aβ)-octahydro-1H-indole-2-carboxylic acid and 6.0 g of potassium bicarbonate in 30 ml of water. The resulting solution is stirred for an additional forty-five minutes at 0° C. and then 2 N sulfuric acid is added to pH 3.5. The oily product is dissolved in 150 ml of diethyl ether and the aqueous layer is extracted with another 150 ml of ether. The combined ether extracts are washed with saturated sodium chloride solution, dried over sodium sulfate, and concentrated to about 40 ml which on cooling yields 2.4 g of white crystals of high purity; mp 103°–104° C. Concentration of the filtrate followed by dilution with warm isopropyl ether gives 2.9 g of additional product; mp 103°-104° C. Recrystallization from ethyl acetate gives an alternate crystalline form; mp 131°-133° C. Infrared (KBr: 1742 (CO$_2$H); 1689 (S-acetyl C=O); 1648, 1592 cm$^{-1}$ (amide C=O).

Anal. Calcd. for C$_{14}$H$_{21}$NO$_4$S: C, 56.17; H, 7.07; N, 4.68. Found: C, 56.41; H, 6.94; N, 4.60.

The (2α, 3aβ, 7aβ)-octahydro-1H-indole-2-carboxylic acid starting material can be prepared by hydrolysis of the ethyl ester prepared as described in Example 1. Thus, a solution of 2.0 g (0.01 mole) of ethyl (2α, 3aβ, 7aβ)-octahydro-1H-indole-2-carboxylate in 25 ml of 15% hydrochloric acid is heated at reflux for four hours and then evaporated to dryness in vacuo. The off-white residue is recrystallized from acetonitrile-ethyl acetate (3:1) yielding 1.7 g of analytically pure product as the hydrochloride salt; mp 186°-187° C. (dec.). Concentration of the filtrate to a low volume and cooling yields an additional 0.2 g of product; mp 184°-186° C.

The free acid is obtained by dissolving 1.2 g of the hydrochloride salt in 10 ml of water and adding 2 N sodium hydroxide solution until pH 6.5. The resulting solution is evaporated to dryness under reduced pressure on a rotary evaporator with a bath temperature of 35° C. The residue is refluxed with 50 ml of acetonitrile and filtered while hot. The solution is concentrated to about 10 ml and cooled yielding 0.5 g; mp 239°-240° C. (dec.). Tlc (MeOH—CH$_3$CN/SiO$_2$) gives a single spot: R$_f$ 0.4.

Anal. Calcd. for C$_9$H$_{15}$NO$_2$: C, 63.88; H, 8.94; N, 8.28. Found: C, 64.13; H, 8.83; N, 8.17.

(b) (2α, 3aβ, 7aβ)-Octahydro-1-[3-(acetylthio)-propanoyl]-1H-indole-2-carboxylic acid can also be prepared as follows. A mixture of (2α, 3aβ, 7aβ)-octahydro-1H-indole-2-carboxylic acid (3.0 g, 0.0177 mole), hexamethyldisilazane (3.0 g, 0.0186 mole) and one drop of chlorotrimethylsilane in 10 ml of acetonitrile is heated at reflux for three hours. The resulting solution is cooled in an ice bath and a solution of 2.9 g (0.0177 mole) of 3-(acetylthio)propanoyl chloride in 5 ml of acetonitrile is added dropwise. A volume of 15 ml of acetonitrile and volatiles is distilled off at atmospheric pressure. The solution is cooled and 0.35 ml of water is added and the mixture is heated at reflux for 5 minutes. The solution is cooled and filtered and then concentrated under reduced pressure to remove the remaining solvent to yield an oil which solidifies upon standing. The residue is dissolved in 60 ml of boiling ethyl acetate. The solution is filtered and cooled yielding 3.0 g of product; mp 131°-133° C.

EXAMPLE 4

Ethyl (2α, 3aβ, 7aβ)-Octahydro-1-[3-(acetylthio)-2-methylpropanoyl]-1H-indole-2-carboxylate.

Utilizing the procedure described in Example 1, ethyl (2α, 3aβ, 7aβ)-octahydro-1-[3-(acetylthio)-2-methylpropanoyl]-1H-indole-2-carboxylate is produced from ethyl (2α, 3aβ, 7aβ)-octahydro-1H-indole-2-carboxylate and 3-(acetylthio)-2-methylpropanoyl chloride. The product is a viscous oil, bp 261.6° C. (748 mmHg). Infrared (film), 1742 (ester C=O), 1690 (S-acetyl C=O), 1640 cm$^{-1}$ (amide C=O). Tlc (acetonitrile/SiO$_2$) single spot, R$_f$ 0.6.

Anal. Calcd. for C$_{17}$H$_{27}$NO$_4$S: C, 59.81; H, 7.97; N, 4.10. Found: C, 59.55; H, 7.86; N, 4.04.

EXAMPLE 5A (2α, 3aβ, 7aβ)-Octahydro-1-[3-(acetylthio)-2-methylpropanoyl]-1H-indole-2-carboxylic Acid, Diastereomer A.

A solution of 2.05 g (0.01 mole) of (2α, 3aβ, 7aβ)-octahydro-1H-indole-2-carboxylic acid hydrochloride in 15 ml of anhydrous pyridine is stirred at 0° C., while 1.81 g (0.01 mole) of 3-(acetylthio)-2-methylpropanoyl chloride is added dropwise over a period of 10 minutes. The stirring is continued for 2 hours, and then the solution is adjusted to pH 3.5 by the slow addition of 15 percent sulfuric acid. The resulting precipitate is dissolved in 100 ml of diethyl ether, and the aqueous phase is extracted with an additional 100 ml of ether. The combined ethereal extracts are washed with saturated sodium chloride solution, dried over sodium sulfate, and then concentrated to 15 ml. After standing overnight 1.4 g of white crystals are obtained by filtration; mp 165°-7° C. Recrystallization from cyclohexane-ethyl acetate (1:1) gives 0.9 g of highly pure diastereomer A; mp 168.5°-170° C. Infrared (IBr): 1742 (COOH), 1689 (S-acetyl C=O), 1648, 1592 cm$^{-1}$ (amide C=O).

Anal. Calcd. for C$_{15}$H$_{23}$NO$_4$S: C, 57.49; H, 7.40; N, 4.47. Found: C, 57.33; H, 7.15; N, 4.36.

EXAMPLE 5B (2α, 3aβ, 7aβ)-Octahydro-1-[3-(acetylthio)-2-methylpropanoyl]-1H-indole-2-carboxylic Acid, Diastereomer B.

After diastereomer A is obtained by filtration, as set forth in Example 5A, 20 ml of isopropyl ether is added to the original filtrate and the solution is concentrated to 15 ml. Upon cooling 0.7 g of additional product; mp 135°-7° C., is obtained. Repeated fractional crystallization alternately from hexane and ethyl acetate gives a pure sample of diastereomer B, as a white solid; mp 151.5°-153.5° C.

EXAMPLE 6A (2α, 3aβ, 7aβ)-Octahydro-1-(3-mercapto-2-methylpropanoyl)-1H-indole-2-carboxylic Acid, Diastereomer A.

(2α, 3aβ, 7aβ)-Octahydro-1-[3-(acetylthio)-2-methylpropanoyl]-1H-indole-2-carboxylic acid (diastereomer A), 1.0 g, is dissolved at room temperature under nitrogen in 5 N ammonia in methanol. This is stirred 2.5 hours and then the solvent is removed at reduced pressure. The residue is taken up in water, acidified with a 10% potassium bisulfate solution, and extracted into ethyl acetate. Drying (magnesium sulfate) and concentration of the organic layer gives diastereomer A of the desired product, which is purified by crystallization from ethyl acetate. The pure A isomer has mp 155°-156° C.

EXAMPLE 6B (2α, 3aβ, 7aβ)-Octahydro-1-(3-mercapto-2-methylpropanoyl)-1H-indole-2-carboxylic Acid, Diastereomer B.

Applying the procedure set forth in Example 5B gives diastereomer B of (2α, 3aβ, 7aβ)-octahydro-1-(3-mercapto-2-methylpropanoyl)-1H-indole-2-carboxylic acid as a white solid, mp 141°-142° C.

SALTS

Sodium (2α, 3aβ, 7aβ)-Octahydro-1-(3-mercapto-2-methyl-propanoyl)-1H-indole-2-carboxylic acid (5 mg) is dissolved in a solution of water (2.5 ml) and an equivalent amount of 1 N sodium hydroxide. The solution is freeze dried to obtain the sodium salt.

Magnesium (2α, 3aβ, 7aβ)-Octahydro-1-(3-mercapto-2-methyl-propanoyl)-1H-indole-2-carboxylic acid (5 mg) magnesium oxide (49.5 mg) and water (10 ml) are stirred with slight heating until complete solution is obtained. Then the solvent is removed by freeze drying to obtain the magnesium salt.

Calcium (2α, 3aβ, 7aβ)-Octahydro-1-(3-mercapto-2-methyl-propanoyl)-1H-indole-2-carboxylic acid (5 mg) is dissolved in a mixture of calcium hydroxide (91 mg) and water (10 ml), and the solution is freeze dried to obtain the calcium salt.

Potassium (2α, 3aβ, 7aβ)-Octahydro-1-(3-mercapto-2-methyl-propanoyl)-1H-indole-2-carboxylic acid (5 mg) is dissolved in a mixture of an equivalent amount of potassium bicarbonate and water (10 ml) and freeze dried to obtain the potassium salt.

EXAMPLE 7

(l)-(2α, 3aβ, 7aβ)-Octahydro-1-[3-(acetylthio)propanoyl]-1H-indole-2-carboxylic Acid.

Following the alternate procedure set forth in Example 3, (l)-(2α, 3aβ, 7aβ)-octahydro-1H-indole-2-carboxylic acid is converted to (l)-(2α, 3aβ, 7aβ)-octahydro-1-[3-(acetylthio)propanoyl]-1H-indole-2-carboxylic acid having mp 110°–112° C., $[\alpha]_D^{23} = -51.0°$ (C=1, methanol). The resolution of the amino acid is described below in Example 15 under the heading, "Resolution of octahydro-1H-indole-2-carboxylic acid."

EXAMPLE 8

(l)-(2α, 3aβ, 7aβ)-Octahydro-1-(3-mercaptopropanoyl)-1H-indole-2-carboxylic Acid.

Following the procedure set forth in Example 6, (l)-(2α, 3aβ, 7aβ)-octahydro-1-[3-(acetylthio)-propanoyl]-1H-indole-2-carboxylic acid is converted to (l)-(2α, 3aβ, 7aβ)-octahydro-1-(3-mercaptopropanoyl)-1H-indole-2-carboxylic acid having mp 168.5°–170° C., $[\alpha]_D^{23} = -68.5°$ (C=1, methanol).

EXAMPLE 9

(2α, 3aβ, 7aβ)-Octahydro-1-[3-(2,2-dimethylpropanoylthio)-2-methylpropanoyl]-1H-indole-2-carboxylic Acid.

A mixture of 2.44 g of 2,2-dimethylpropanoic acid, 1,1'-carbonyldiimidazole and 50 ml of dry dimethylformamide is prepared and stirred for 1 hour at room temperature until the evolution of gas ceases. A solution of racemic (2α, 3aβ, 7aβ)-octahydro-1-(3-mercapto-2-methylpropanoyl)-1H-indole-2-carboxylic acid (diastereomer A) and 2.05 g of triethylamine in 20 ml of dimethylformamide is then added and this mixture is stirred for 18 hours at 25° C. The solvent is removed at reduced pressure and the residue is treated with water, acidified with dilute hydrochloric acid and extracted with ethyl acetate. The organic layer is washed with a saturated sodium chloride solution, dried (magnesium sulfate) and concentrated to dryness to give the desired product. This is purified by recrystallization from ethyl acetate and has mp 134°–136° C.

EXAMPLE 10

(2α, 3aβ, 7aβ)-Octahydro-1-[3-(benzoylthio)-2-methyl-propanoyl]-1H-indole-2-carboxylic Acid (Diastereomer A) t-Butylamine Salt.

Following the procedure of Example 9, but substituting benzoic acid for 2,2-dimethylpropanoic acid, racemic (2α, 3aβ, 7aβ)-octahydro-1-[3-(benzoylthio)-2-methylpropanoyl]-1H-indole-2-carboxylic acid (diastereomer A) is obtained as an oil. This is purified by preparing a salt with t-butylamine, which after recrystallization from acetonitrile has mp 164°–166° C. (dec.).

EXAMPLE 11

(l)-(2α, 3aβ, 7aβ)-Octahydro-1-[3-(benzoylthio)-2-methyl-propanoyl]-1H-indole-2-carboxylic Acid (Diastereomer A).

A solution of 1.8 g (l)-(2α, 3aβ, 7aβ)-octahydro-1H-indole-2-carboxylic acid and 2.5 g of pyridine in 20 ml of tetrahydrofuran is cooled to 0°–5° C. and treated dropwise with (l)-3-(benzoylthio)-2-methylpropionyl chloride. The mixture is stirred for 2 hours at 0°–5° C., and then is concentrated to remove the solvent. The residue is treated with water, acidified with 6 N sulfuric acid and extracted with ethyl acetate. The organic layer is washed with a saturated sodium chloride solution, dried (magnesium sulfate) and concentrated to dryness. The residue which partly crystallizes is triturated with ethyl acetate and filtered to separate the desired product. This is purified by recrystallization from ethyl acetate and has mp 184.5°–185.5° C., $[\alpha]_D^{25} = -135.6°$ (C=1, methanol).

EXAMPLE 12

(l)-(2α, 3aβ, 7aβ)-Octahydro-1-(3-mercapto-2-methylpropanoyl)-1H-2-carboxylic Acid (Diastereomer A), Dicyclohexylamine Salt.

Following the procedure of Example 6, but substituting (l)-(2α, 3aβ, 7aβ)-octahydro-1-[3-(benzoylthio)-2-methylpropanoyl]-1H-2-carboxylic acid (diastereomer A) for (2α, 3aβ, 7aβ)-octahydro-1-[3-(acetylthio)-2-methylpropanoyl]-1H-indole-2-carboxylic acid, (l)-(2α, 3aβ, 7aβ)-octahydro-1-(3-mercapto-2-methyl-propanoyl)-1H-2-carboxylic acid is obtained. This material is purified as the dicyclohexylamine salt; mp 145°–148° C., $[\alpha]_D^{23} = -53.5°$ (C=1, methanol).

EXAMPLE 13

(2α, 3aβ, 7aβ)-Octahydro-1-[3-(propanoylthio)-2-methyl-propanoyl]-1H-indole-2-carboxylic Acid, (Diastereomer A).

Following the procedure of Example 9, and substituting propionic acid for 2,2-dimethylpropanoic acid, (2α, 3aβ, 7aβ)-octahydro-1-[3-(propanoylthio)-2-methyl-propanoyl]-1H-indole-2-carboxylic acid (diastereomer A) can be obtained. It has mp 170°–172° C. after recrystallization from acetonitrile.

EXAMPLE 14

(2α, 3aβ, 7aβ)-1-[2-[(1-Carboethoxy-3-phenylpropyl)amino]-1-oxopropyl]octahydro-1H-indole-2-carboxylic Acid, Hydrochoride.

A solution of 5.57 g of the S,S-isomer of ethyl α-[(1-carboxyethyl)amino]benzenebutanoate hydrochloride in 55 ml of dichloromethane is treated with 2.5 ml of triethylamine, followed by 3.0 g of 1,1'-carbonyl-diimidazole, and the solution stirred at room temperature for 1 hour. To this solution is then added 2.5 ml of triethylamine followed by 4.61 g of t-butyl (dl)-octahydro-1H-indole-2-carboxylate, hydrochloride, and the mixture stirred at room temperature overnight. The mixture is filtered, and the filtrate washed with 0.1 N acetic acid, water, and then saturated sodium chloride solution. Drying over magnesium sulfate and removal of the solvent under reduced pressure gives 8.14 g of the crude t-butyl ester of the product as an oil.

A solution of 7.94 g of this t-butyl ester in 75 ml of dichloromethane is saturated with hydrogen chloride gas and left standing at room temperature overnight. The solvent is removed under reduced pressure and the resulting foam triturated with ether and collected. This material is dissolved in water, filtered, and freeze-dried. There is obtained 6.6 g of the product as a mixture of isomers, mp 112°–150° C., $[\alpha]_D^{23} = +6.2°$ (1.05% in 1 N hydrochloric acid).

The intermediate ethyl α-[(1-carboxyethyl)amino]-benzenebutanoate hydrochloride used in this preparation may be prepared in the following manner. A solution of 2.0 g of t-butyl L-alanine and 3.78 g of ethyl 2-bromo-4-phenylbutanoate in 25 ml of dimethylformamide is treated with 1.8 ml of triethylamine and the solution is heated at 70° C. for 18 hours. The solvent is removed at reduced pressure and the residue is mixed with water and extracted with ethyl ether. The organic layer is washed with water and dried over magnesium sulfate. Concentration of the solvent at reduced pressure gives the oily t-butyl ester of the intermediate which is found to be sufficiently pure by gas liquid chromatography for further use.

A solution of 143.7 g of this t-butyl ester in 630 ml of trifluoroacetic acid is stirred at room temperature for one hour. The solvent is removed at reduced pressure and the residue is dissolved in ethyl ether and again evaporated. This operation is repeated. Then the ether solution is treated dropwise with a solution of hydrogen chloride gas in ethyl ether until precipitation ceases. The solid is collected by filtration and is a mixture of diastereoisomers, mp 153°–165° C., $[\alpha]_D^{23} = +3.6°$ (c=1, methanol).

In order to separate the preferred S,S isomer, a suspension of 10.0 g of the mixture in 200 ml of methylene chloride is stirred at room temperature for five minutes and filtered; the solid material, mp 202°–204° C. (dec.), $[\alpha]_D^{23} = -29.3°$ (c=1, methanol) is the less preferred diastereoisomer having the R,S configuration (S referring to the portion derived from L-alanine). The preferred S,S-diastereoisomer can be recovered from the filtrate after concentration and trituration of the residue with ether. It has mp 137°–139° C., $[\alpha]_D^{23} = +31.3°$ (c=1, methanol).

The other intermediate used in this preparation, t-butyl (dl)-octahydro-1H-indole-2-carboxylate hydrochloride, is prepared as follows. A solution of 20.0 g of (dl)-octahydro-1H-indole-2-carboxylic acid in 200 ml of dioxane contained in a pressure vessel is treated with 20 ml of concentrated sulfuric acid and 120 g of isobutylene and kept at 20° C. for 26 hours with stirring. The mixture is then poured into ice water containing 60 ml of 50% sodium hydroxide solution, and the mixture is extracted three times with ether. The ether is washed with water, saturated sodium chloride solution, and then dried over magnesium sulfate. The ether solution is treated with isopropanolic hydrogen chloride solution, and then stripped to an oil which slowly crystallizes on standing. The solid is collected and washed with ether giving 11.33 g of the ester hydrochloride, mp 112°–116° C.

EXAMPLE 15

(2α, 3aβ, 7aβ)-1-[2-[(1-Carboxy-3-phenylpropyl)amino]-1-oxopropyl]octahydro-1H-indole-2-carboxylic Acid.

A solution of 2.0 g of the isomeric mixture of (2α, 3aβ, 7aβ)-1-[2-[(1-carboethoxy-3-phenylpropyl)amino]-1-oxopropyl]octahydro-1H-indole-2-carboxylic acid hydrochloride, (prepared as in Example 14), in 10 ml of water and 10 ml of ethanol is treated with 0.57 g of sodium hydroxide. The solution is left at room temperature for 4 hours with occasional swirling. The solution is concentrated under reduced pressure and the residue taken up in water. The pH is adjusted to 3.4 with dilute hydrochloric acid and the precipitated solid is collected to give 0.6 g of the product as a mixture of isomers, mp 135°–137° C. (dec.), $[\alpha]_D^{23} = +6.2°$ (0.53%, 1:1 methanol/1 N hydrochloric acid).

Resolution of octahydro-1H-indole-2-carboxylic acid.

A solution of 20.0 g of racemic (2α, 3aβ, 7aβ)-octahydro-1H-indole-2-carboxylic acid in 200 ml of water is cooled in an ice bath and treated dropwise during 1.5 hours simultaneously but separately with 14.4 ml of benzoyl chloride and 120 ml of 2 N sodium hydroxide solution, keeping the pH between 6 and 8. The solution is stirred for an additional 30 minutes and the pH is adjusted to 1.8 with 1 N hydrochloric acid. Racemic N-benzoyl-(2α, 3aβ, 7aβ)-octahydro-1H-indole-2-carboxylic acid precipitates and is collected by filtration. Recrystallization from aqueous ethanol gives pure product, mp 191°–193° C.

This compound, 87.75 g, is added to a solution of 38.9 g, of (l)-α-phenylethylamine in 700 ml of methanol to form a solution. This is diluted with 1250 ml of ethyl acetate and seeded with a crystal of the resolved salt. The mixture begins to precipitate the desired salt. After standing 18 hours at 5° C., the salt, collected by filtration, has mp 212°–215° C. (dec.) and $[\alpha]_D^{23} = -49.4°$ (C=1, methanol). Recrystallization from a 2:1 mixture of ethyl acetate and methanol gives product with the same mp and rotation.

The levorotatory salt, 48.2 g, is suspended in a mixture of 884 ml of water and 353 ml of methanol and acidified with dilute hydrochloric acid to pH 2. After 15 minutes, the initial solid dissolves and a new solid separates. Water, 430 ml, is added and the (l)-N-benzoyl-(2α, 3aβ, 7aβ)-octahydro-1H-indole-2-carboxylic acid is collected by filtration, mp 169°–171° C., $[\alpha]_D^{23}= -51.4°$ (C=1, methanol).

A suspension of the (1)-benzoate in 200 ml of 6 N hydrochloric acid is heated at reflux for 4 hours. The resulting solution is diluted with 100 ml of water and cooled. Filtration removes precipitated benzoic acid. The filtrate is extracted with chloroform and the pH of the aqueous layer is adjusted to 6.5 with dilute sodium hydroxide solution. Concentration of this to dryness gives a solid which is ground and extracted with anhydrous ethanol. Concentration of the ethanol extract gives (1)-(2α, 3aβ, 7aη)-octahydro-1H-indole-2-carboxylic acid which may be purified by passing it through an ion exchange resin in the acid form and eluting with 2 N ammonium hydroxide, isolating the solid and recrystallizing this from anhydrous ethanol. The pure (1)-amino acid has mp 265°–266° C. (dec.), $[\alpha]_D^{25}= -48.5°$ (C=1, methanol).

EXAMPLE 16

(2α, 3aβ, 7aβ)-1-[2-[(1-Carboethoxy-3-phenylpropyl)amino]-1-oxopropyl]octahydro-1H-indole-2-carboxylic Acid hydrochloride, (S,S,S-isomer).

A solution of 1.23 g of the S,S-isomer of ethyl [(1-carboxyethyl)amino]benzenebutanoate hydrochloride, 0.92 g of t-butyl (1)-octahydro-1H-indole-2-carboxylate, 0.53 g of hydroxybenzotriazole, monohydrate, and 0.54 ml of triethylamine in 15 ml of N,N-dimethylformamide is cooled in ice and treated dropwise with a solution of 0.8 g of N,N'-dicyclohexylcarbodiimide in 2 ml of N,N-dimethylformamide. After stirring for 1 hour at 0° C., the cooling is removed and the mixture allowed to stir at room temperature overnight.

The mixture is filtered to remove dicyclohexylurea, and the N,N-dimethylformamide removed by distillation under high vacuum. The residue is taken up in ethyl acetate, washed two times with saturated sodium bicarbonate solution and then with saturated sodium chloride solution. Drying over magnesium sulfate and removal of the solvent under reduced pressure leaves an oil. This is taken up in ether, filtered, and the ether is removed under reduced pressure leaving 1.9 g of the crude t-butyl ester of the product as an oil.

A solution of 0.63 g of this t-butyl ester in 6 ml of dichloromethane is saturated with hydrogen chloride gas and allowed to stir at room temperature overnight. The solvent is removed under reduced pressure, more dichloromethane is added, and the solvent removed again. The residue is taken up in dichloromethane, treated with charcoal, and filtered. Removal of the solvent under reduced pressure gives a foam. This is triturated with ether and collected giving 0.35 g (58% yield) of the product, $[\alpha]_D^{23}= -29.7°$ (1.01%, 1:1 methanol/1 N hydrochloric acid).

The intermediate t-butyl (1) octahydro-1H-indole-2-carboxylate used in this preparation is prepared as follows. A solution of 14.23 g of (1) octahydro-1H-indole-2-carboxylic acid (prepared as described in Example 3) in 150 ml of dioxane contained in a pressure vessel is treated with 15 ml of concentrated sulfuric acid and 84 g of isobutylene and kept at 20° C. for 20 hours with stirring. The mixture is then poured into ice water containing 45 ml of 50% sodium hydroxide solution and the mixture is extracted three times with ether. The ether is washed with water, then saturated sodium chloride solution. Drying over magnesium sulfate and removal of the ether under reduced pressure gives 14.4 g of the desired t-butyl ester as an oil, $[\alpha]_D^{23}= -27.6°$ (1.1% in methanol).

EXAMPLE 17

(2α,3aβ,7aβ)-1-[2-[(1-Carboxy-3-phenylpropyl)amino]-1-oxopropyl]octahydro-1H-indole-2-carboxylic acid (S,S,S-isomer).

Hydrolysis according to the procedure of Example 15 but substituting (2α,3aβ,7aβ)-1-[2-[(1-carboethoxy-3-phenylpropyl)amino]-1-oxopropyl]octahydro-1H-indole-2-carboxylic acid (S,S,S-isomer) for the isomer mixture described in Example 15, gives the crude product. Purification by ion exchange using Dowex 1-X2, gives pure product, mp 138°–140° C. (dec.), $[\alpha]_D^{23}= -37.6°$ (c=1, 1 N hydrochloric acid).

EXAMPLE 18

1000 tablets each containing 100 mg of (2α,3aβ,7aβ)-octahydro-1-(3-mercapto-2-methylpropanoyl)-1H-indole-2-carboxylic acid are produced from the following ingredients.

| | |
|---|---|
| (2α, 3aβ, 7aβ)-Octahydro-1-(3-mercapto-2-methyl-propanoyl)-1H-indole-2-carboxylic acid | 100 g |
| Corn Starch | 50 g |
| Gelatin | 7.5 g |
| Avicel (microcrystalline cellulose) | 25 g |
| Magnesium Stearate | 2.5 g |

The (2α,3aβ,7aβ)-octahydro-1-(3-mercapto-2-methylpropanoyl)-1H-indole-2-carboxylic acid and corn starch are admixed with an aqueous solution of the gelatin. The mixture is dried and ground to fine powder. The Avicel and then the magnesium stearate are admixed with the granulation. This is then compressed in a tablet press to form 1000 tablets each containing 100 mg of active ingredients.

EXAMPLE 19

1000 tablets each containing 200 mg of (2α3aβ,7aβ)-octahydro-1-(3-mercapto-2-methylpropanoyl)-1H-indole-2-carboxylic acid are produced from the following ingredients.

| | |
|---|---|
| (2α, 3aβ, 7aβ)-Octahydro-1-(3-mercapto-2-methyl-propanoyl)-1H-indole-2-carboxylic acid | 200 g |
| Lactose | 100 g |
| Avicel | 150 g |
| Corn Starch | 50 g |
| Magnesium Stearate | 5 g |

The (2α,3aβ,7aβ)-octahydro-1-(3-mercapto-2-methylpropanoyl)-1H-indole-2-carboxylic acid, lactose and Avicel are admixed, then blended with the corn starch. Magnesium stearate is added. The dry mixture is compressed in a tablet press to form 1000, 505 mg tablets each containing 200 mg of active ingredient. The tablets are coated with a solution of Methocel E 15 (methyl cellulose) including as a color a lake containing yellow No. 6.

EXAMPLE 20

Two piece No. 1 gelatin capsules each containing 250 mg of (2α,3aβ,7aβ)-octahydro-1-(3-mercapto-2-methylpropanoyl)-1H-indole-2-carboxylic acid are filled with a mixture of the following ingredients.

| | |
|---|---|
| (2α, 3αβ, 7αβ)-Octahydro-1-(3-mercapto-2-methyl-propanoyl)-1H-indole-2-carboxylic acid | 250 mg |
| Magnesium Stearate | 7 mg |
| USP Lactose | 193 mg |

EXAMPLE 21

An injectable solution is produced as follows:

| | |
|---|---|
| (2α, 3αβ, 7αβ)-Octahydro-1-(3-mercapto-2-methyl-propanoyl)-1H-indole-2-carboxylic acid, sodium salt | 500 g |
| Methyl Paraben | 5 g |
| Propyl Paraben | 1 g |
| Sodium Chloride | 25 g |
| Water for Injection q.s. | 5 l |

The active substance, preservatives and sodium chloride are dissolved in 3 liters of water for injection and then the volume is brought up to 5 liters. The solution is filtered through a sterile filter and aseptically filled into presterilized vials which are then closed with presterilized rubber closures. Each vial contains 5 ml of solution in a concentration of 100 mg of active ingredient per ml of solution for injection.

We claim:

1. A octahydro-1-(ω-mercaptoalkanoyl)-1H-indole-2-carboxylic acid compound having the formula

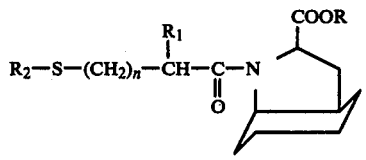

wherein R is hydrogen or lower alkyl; $R_1$ is hydrogen, lower alkyl, or benzyl; $R_2$ is hydrogen or

where $R_3$ is lower alkyl, phenyl, substituted phenyl having 1 or 2 substituents selected from the group consisting of fluorine, chlorine, bromine, lower alkyl or alkoxy; and n is 0 or 1; wherein lower alkyl and lower alkoxy include straight or branched groups having 1 to 4 carbon atoms and pharmaceutically acceptable salts of the compounds when R is hydrogen.

2. A substituted octahydro-1-(3-mercaptoalkanoyl)-1H-indole-2-carboxylic acid compound according to claim 1 having the formula

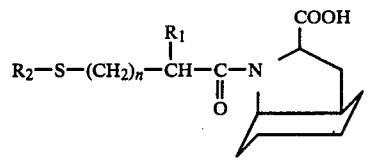

and pharmaceutically acceptable salts thereof; where $R_1$ is hydrogen, or lower alkyl having 1 to 3 carbon atoms; $R_2$ is hydrogen or

where $R_3$ is lower alkyl having 1 to 3 carbon atoms, phenyl, and n is 0 or 1.

3. A substituted octahydro-1-(3-mercaptopropanoyl)-1H-indole-2-carboxylic acid compound according to claim 2 wherein $R_1$ is hydrogen or methyl; $R_2$ is hydrogen or

where $R_3$ is methyl, or phenyl and pharmaceutically acceptable basic salts thereof.

4. The compound according to claim 3 which is octahydro-1-[3-(acetylthio)-2-methylpropanoyl]-1H-indole-2-carboxylic acid and pharmaceutically acceptable basic salts thereof.

5. The compound according to claim 3 which is octahydro-1-(3-mercapto-2-methylpropanoyl)-1H-indole-2-carboxylic acid and pharmaceutically acceptable basic salts thereof.

6. The compound according to claim 5 which is (2α,-3αβ,7αβ)-octahydro-1-(3-mercapto-2-methyl-propanoyl)-1H-indole-2-carboxylic acid and the pharmaceutically acceptable basic salts thereof.

7. The compond according to claim 6 which is (2α,-3αβ,7αβ)-octahydro-1-(3-mercapto-2-methyl-propanoyl)-1H-indole-2-carboxylic acid, diastereomer A and the pharmaceutically acceptable basic salts thereof.

8. The compound according to claim 6 which is (1)-(2α,3αβ,7αβ)-octahydro-1-(3-mercapto-2-methyl-propanoyl)-1H-indole-2-carboxylic acid, diastereomer A and the pharmaceutically acceptable basic salts thereof.

9. The compound according to claim 3 which is octahydro-1-(3-mercaptopropanoyl)-1H-indole-2-carboxylic acid and pharmaceutically acceptable basic salts thereof.

10. The compound according to claim 3 which is octahydro-1-[3-(acetylthio)propanoyl]-1H-indole-2-carboxylic acid and pharmaceutically acceptable basic salts thereof.

11. A hypertensive pharmaceutical composition comprising a substituted octahydro-1-(3-mercaptoalkanoyl)1-indole-2-carboxylic acid compound according to claim 1 or a pharmaceutically acceptable salt thereof and a pharmaceutically acceptable carrier.

12. A method of treating hypertension by administering an effective amount of a substituted octahydro-1-(3-mercaptoalkanoyl)-1-indole-2-carboxylic acid compound according to claim 1 or a pharmaceutically acceptable salt thereof.

* * * * *